United States Patent
Jaynes

(10) Patent No.: US 6,514,692 B2
(45) Date of Patent: *Feb. 4, 2003

(54) METHOD FOR TREATMENT OF IMMUNODEFICIENCY VIRUS INFECTION

(75) Inventor: Jesse M. Jaynes, Raleigh, NC (US)

(73) Assignee: Demegen, Inc., Pittsburgh, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/269,882

(22) PCT Filed: Oct. 3, 1997

(86) PCT No.: PCT/US97/17522

§ 371 (c)(1), (2), (4) Date: Apr. 2, 1999

(87) PCT Pub. No.: WO98/14201

PCT Pub. Date: Apr. 9, 1998

(65) Prior Publication Data

US 2002/0155132 A1 Oct. 24, 2002

Related U.S. Application Data

(60) Provisional application No. 60/027,628, filed on Oct. 4, 1996.

(51) Int. Cl.[7] .......................... C12Q 1/70; A61K 39/00; A61K 39/21

(52) U.S. Cl. .................. 435/5; 424/184.1; 424/187.1; 424/188.1; 424/204.1; 424/207.1; 424/208.1

(58) Field of Search ............................ 424/184.1, 187.1, 424/185.1, 204.1, 207.1, 208; 514/12, 13, 14, 15; 435/5

(56) References Cited

U.S. PATENT DOCUMENTS

| | | |
|---|---|---|
| 4,355,104 A | 10/1982 | Hultmark et al. |
| 4,520,016 A | 5/1985 | Hultmark et al. |
| 4,810,777 A | 3/1989 | Zasloff |
| 5,861,478 A * | 1/1999 | Jaynes .................. 530/324 |

FOREIGN PATENT DOCUMENTS

| | | |
|---|---|---|
| WO | 9012866 | 11/1990 |
| WO | 9603519 | 2/1996 |
| WO | 9603522 | 2/1996 |

OTHER PUBLICATIONS

Haynes et al; Update on the issues of HIV vaccine development; Ann. Med.; vol. 28; pp. 39–41, 1996.*

Yarchoan et al.; Correlations between the in vitro and in vivo . . . ; J. Enzyme Inhibition; vol. 6; pp. 99–111, 1992.*

Gait et al.; Progress in anti–HIV structure based drug design; TIBTECH; vol. 13; pp. 430–438, 1995.*

Arrowood et al., "Hemolytic Properties of Lytic Peptides Active Against the Sporozoites of *Cryptosporidium parvum*", *J. Protozool.*, 38(6):161S–163S (Nov.–Dec. 1991).

De Lucca et al., "Comparison of Synthetic Peptide D4E1 and Cecropin a on Fungal Viability", *Abstracts of the General Meeting of the American Society for Microbiology*, May 19, 1996. vol. 96, p. 144, Abstract No. A–65.

Jaynes, Jesse M., "Lytic Peptides Portend and Innovative Age in the Management and Treatment of Human Disease", *DN&P*, 3(2):69–78 (Mar. 1990).

Jaynes et al., "In Vitro Cytocidal Effect of Lytic Peptides on Several Transformed Mammalian Cell Lines", *Peptide Research* 2 (1989) pp. 157–160.

* cited by examiner

Primary Examiner—Hankyel T. Park
Assistant Examiner—Stacy S. Brown
(74) *Attorney, Agent, or Firm*—Rothwell, Figg, Ernst & Manbeck

(57) ABSTRACT

The present invention relates to methods for treating immunodeficiency virus infection in an infected animal comprising administering an effective amount of a lytic peptide.

5 Claims, 2 Drawing Sheets

METHOD FOR TREATMENT OF IMMUNODEFICIENCY VIRUS INFECTION

This application is the national phase of International Application PCT/US97/17522, filed Oct. 3, 1997, which claims the benefit of the filing date of United States provisional application 60/027,628, filed Oct. 4, 1996.

FIELD OF THE INVENTION

This invention pertains to the field of antiviral therapy and to peptide chemistry. More particularly, the invention relates to lytic peptides having significant anti-viral activity.

BACKGROUND OF THE INVENTION

Naturally occurring lytic peptides play an important, if not critical, role as immunological agents in insects, and appear to provide defense functions in a range of other animals as well. These peptides destroy prokaryotic and other non-host cells by disrupting the cell membrane, thereby promoting cell lysis. Common features of these naturally occurring lytic peptides include an overall basic charge, a small size (23–39 amino acid residues), and the ability to form amphipathic α-helices or β-pleated sheets. Another feature found in some lytic peptides is a hydrophobic tail, a non-amphipathic sequence of hydrophobic amino acids of varying length located at one end of the peptide.

Several groups of amphipathic peptides have been identified, including cecropins (originally described in U.S. Pat. No. 4,355,104 and 4,520,016 to Hultmark et al.), defensins, sarcotoxins, melittin, and magainins (described in U.S. Pat. No. 4,810,777 to Zasloff). Each of these groups of peptides is distinguished by sequence and secondary structure characteristics.

The mechanism of peptide-induced cell lysis relies on the ordered secondary conformation and positive charge density of the peptide. Several hypotheses for explaining the mechanism by which these peptides exert their effect have been advanced. For example, the peptides may form ion channels or pores which extend through the cell membrane, and result in osmotically induced cytolysis.

Active synthetic analogs of naturally occurring lytic peptides have been produced and tested in vitro against a variety of prokaryotic and eukaryotic cell types (see for example Arrowood, et al., *J. Protozool.*, 38: 161s (1991); Jaynes, et al., *FASEB J.*, 2: 2878 (1988)), including: gram positive and gram negative bacteria, fungi, yeast, protozoa, and neoplastic or transformed mammalian cells. The studies have demonstrated that synthetic peptide analogs can have higher levels of lytic activity for different types of cells than the naturally occurring peptides. A discussion of lytic peptides, both naturally-occuring and synthetic, can be found in Jaynes, "Lytic peptides, use for growth, infection and cancer," WO 90/12866 (incorporated herein by reference). This reference sets out the defining qualities of lytic peptides and sets out several sequences of active synthetic lytic peptides.

The specificity of the peptide action can depend upon the concentration of the amphipathic peptide and the type of membrane with which it interacts. Jaynes, J. M., et al., *Peptide Research*, 2: 157 (1989) discuss the altered cytoskeletal characteristics of transformed or neoplastic mammalian cells that make them susceptible to lysis by such peptides. Normal, human non-transformed cells remain unaffected at a given peptide concentration, while transformed cells were lysed; however, when normal cells were treated with the cytoskeletal inhibitors cytochalasin D or colchicine, sensitivity to lysis increased. The experiments show that the action of amphipathic peptides on normal mammalian cells is limited. This resistance to lysis was most likely due to the well-developed cytoskeletal network of normal cells. In contrast, transformed cell lines, which have well-known cytoskeletal deficiencies, were sensitive to lysis. Because of differences in cellular sensitivity to lysis, lytic peptide concentration can be manipulated to effect lysis of one cell type but not another at the same situs within an organism.

The virus responsible for AIDS (Acquired Immunodeficiency Syndrome) commonly called HIV (Human Immunodeficiency Virus), is more appropriately called HTLV III for Human T-Cell Leukemia Virus and, thus, is one of several retroviruses that have recently been described as responsible for some types of leukemia. AIDS has been recognized clinically, as a unique syndrome, since 1981. The hallmark of this disease is a quantitative reduction in the T-helper-cell population resulting in a greatly increased sensitivity to infectious disease, with the ultimate outcome of death by opportunistic infection a foreordained consequence of virus infection. The virus contains RNA and, as a retrovirus, possesses several unique enzymes which ultimately allow for the integration of the viral genome into the host's heredity in a DNA form. The virus can remain "silent" for many years until, under certain conditions, the viral genome is activated and infectious virus is produced in massive numbers resulting in the eventual depletion of the victim's T-helper-cell population. This component of the immune system is integral to fighting the infections that are encountered on a daily basis. HIV infection is very difficult to treat due in part to its highly variable and mutable coat characteristics, which make traditional vaccine treatment ineffective.

SUMMARY OF THE INVENTION

The present invention relates to a method for treating animals infected with a retrovirus or enveloped virus. The method comprises treating the infected animal with a lytic peptide at concentrations that are lethal to virus or virus-infected cells, yet are sub-lethal to healthy cells. A further embodiment of this invention is the treatment of a retrovirus or enveloped virus-infected animal with a dose of lytic peptide that is sub-lethal to the virus or virus-infected cells, but results in the infected cell producing virus particles that are non-infective.

DETAILED DESCRIPTION OF THE INVENTION

Figure 1:
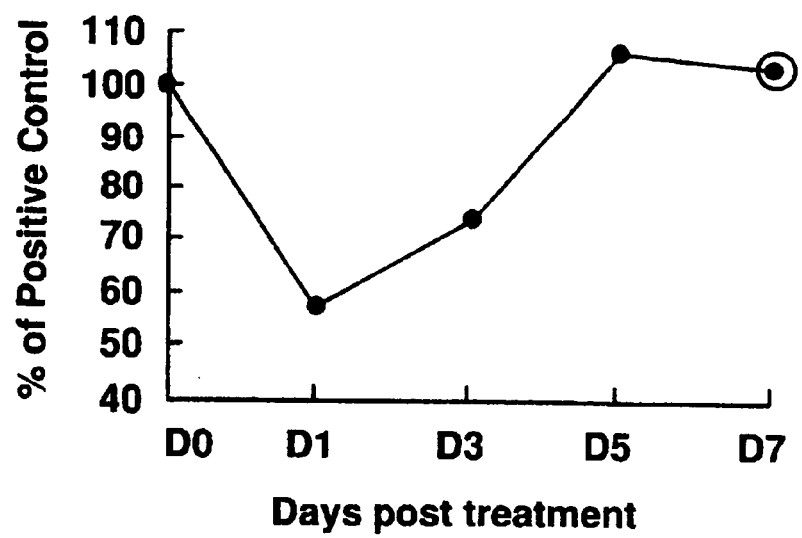
FIG. 1 shows p26 levels of chronically infected CrFK cells with a single lytic peptide treatment.

At appropriate doses, peptidyl MIMs (Membrane Interactive Molecules), that is, lytic peptides of natural or synthetic origin, will eliminate retrovirus such as the immunodeficiency viruses FIV, SIV and HIV, and enveloped virus generally, and kill infected cells. Virus infected cells often exhibit syncytium formation and cytoskeletal aberrations. The presence of cytoskeletal aberrations suggests that infected cells will have increased sensitivity to lysis by lytic peptides. It has, in fact, been demonstrated by the inventor that increased lysis and reduction in viral titer occurred in cells infected with Herpes Simplex Virus II (HSV II) following treatment with certain amphipathic peptides. This occurs at peptide concentrations significantly below levels toxic to normal cells, preferably from 0.05 mg/kg to 15 mg/kg of body weight of the treated subject/day.

However, merely destroying infected cells via the known effect of lytic peptides against cells having impaired cytoskeletal structures does not appear to be the mechanism involved in the antiviral effect of lytic peptides, which is, in fact, fundamentally different from that seen against other cell types. Lytic peptides actually block cell-to-cell transmission of HIV at peptide concentrations that are sub-lethal to non-infected cells. In fact, if immunodeficiencyvirus-infected cells are treated with amounts of the peptides that do not completely eliminate the virus, the virus which subsequently arises from these treated cultures is completely non-infectious. This shows a completely unexpected effect of lytic peptides against virus and virus-infected cells, one that perhaps acts at the DNA level by regulation rather than at the cellular level by lysis. This effect can be expected with retrovirus, lentivirus, herpesvirus or enveloped virus generally.

What is so remarkable about the activity of peptidyl-MIMs, on these types of viruses, is that they exert their effect at such a low concentration, far below that necessary to see cell loss as an explanation for the reduction of virus. As stated above, this implicates more than the lytic action that is the known property of these peptides. Also, at the same time, as we reduce virus number and actually generate non-infectious virus,it would be possible control disease-causing opportunistic infections which are actually the entities responsible for death of individuals infected by HIV, because the peptidyl-MIMs are quite active against all these major pathogens. The peptidyl-MIMs thus have profound implications in controlling retroviral infections.

The medical potential of this effect is enormous. In the embodiment directed towards treatment of immunodeficiency virus infection, infected individuals that were treated with the lytic peptides would produce defective virus that then would act as an immune stimulator. Since the virus is non-infectious, it would not spread any further and would no longer kill those important immune cells that are left and are involved in conferring immunity. This would give the infected person time to mount a cellular defense and they would, in effect, immunize themselves against, and ultimately be resistant to, the virus. Judicial use of the peptides may even keep people from being infected, in that they have been found to lead to the production of non-infective viral particles at doses that are sub-lethal to the virus or infected cells, thus limiting or preventing transmission of the disease between individuals. Also, the peptides could be used to produce non-infectious virus for vaccine development by in vitro methods.

A subject, particularly a mammalian or human subject, infected with a retrovirus which causes an immunodeficient condition, such as FIV or HIV, or a subject who is at risk of becoming infected, can be treated with peptidyl-MIMS which are administered daily. In a preferred embodiment, a composition containing the peptide of choice at a concentration of about 1 to 10 mg/kg of body weight in a formulation suitable for injection would be administered once a day to reduce the in vivo replication of the virus in the subject being treated. A preferred class of peptidyl-MIMs are those that have a β-pleated-sheet secondary configuration and having no hydrophobic tail (i.e. no terminal hydrophobic regions). Peptidyl-MIMs having this kind of structure have been found to have particularly high antiviral activity. A preferred peptide in this class is D4E1, a peptide having the amino acid sequence FKLRAKIKVRLRAKIKL [SEQ. ID. NO. 1]. Other peptide classes are also useful for use with this method, however. A preferred peptidyl-MIM having an α-helical structure and a hydrophobic tail at the carbxy terminus is D2A21, a peptide having the amino acid sequence FAKKFAKKFKKFAKKFAKFAFAF [SEQ. ID. NO. 2]. The invention is not limited to the use of any particular peptide, and the person of ordinary skill in the art will be able to select appropriate peptides for use in the claimed methods. Where the subject is also affected by an opportunistic infection such as a lung infection, other routes of administration of the peptide (such as aerosol) would provide additional benefit.

Because the peptides cause chronically-infected cells to produce non-infectious virus, early treatment would greatly reduce the virus load for a particular subject. In addition the defective virus which are produced by chronically infected cells would provide a source of antigen which would be available to the subject's immune system for developing antibodies.

Another application of this method is for the production of attenuated virus for a vaccine. Incubation in vitro of virus-infected cell lines with appropriate concentrations of active peptidyl-MIMs (i.e. concentrations sub-lethal to both virus and infected cells) would lead to the production by the cell culture of non-infectious virus. This non-infectious virus could be used as a vaccine, or as an immune challenge to cause the production of antibodies useful as an immune serum.

EXAMPLE 1

Inhibition of HIV by Lytic Peptides

Figure 2:
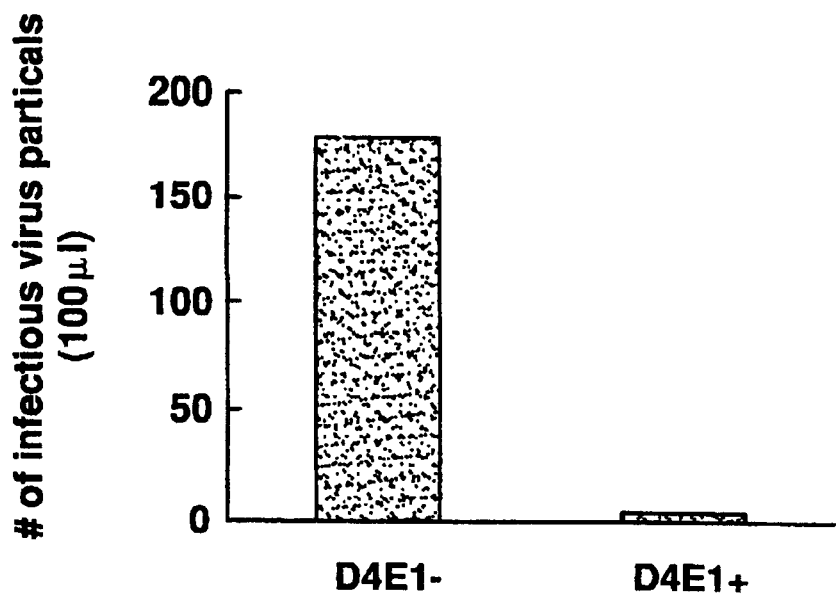
FIG. 2 shows reduction in infectivity of FIV-Petaluma by lytic peptide treatment.
Figure 3:
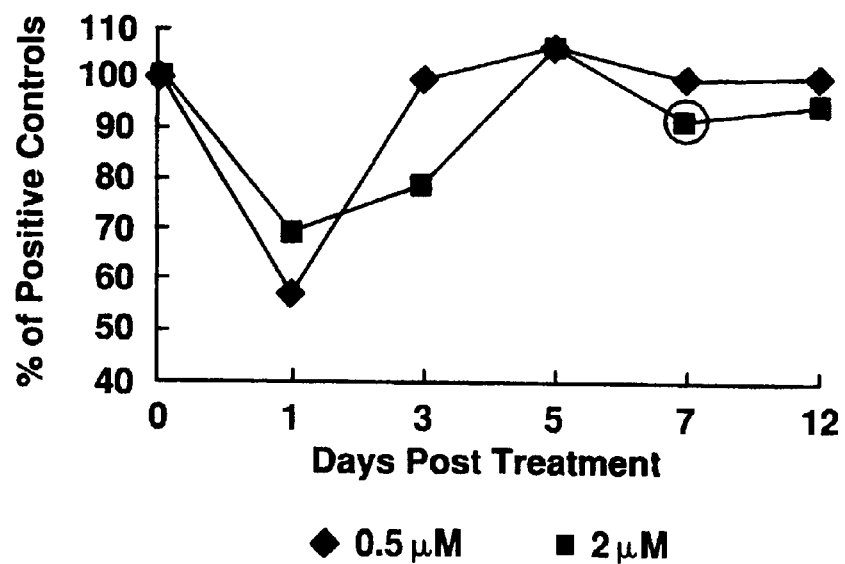
FIG. 3 shows p26 levels of chronically infected CrFK cells with a single lytic peptide treatment, at two different concentrations.
Figure 4:
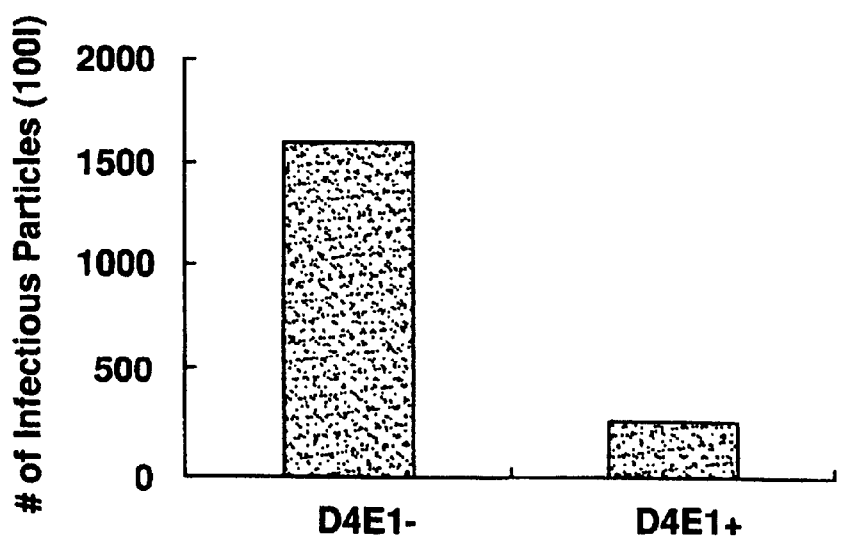
FIG. 4 shows a second experiment showing reduction in infectivity of FIV-Petaluma by lytic peptide treatment.

ME180 cells, a cervical epithelial cell line, were obtained from the American Type Culture Collection. These cells were thawed from liquid nitrogen and grown in RPMI 1640 medium supplemented with 10t fetal bovine serum, glutamine and antibiotics. The cells were adherent and were trypsinized (0.5% trypsin in HBSS) to remove them from the flask for passaging and use in assays. For use in the microtiter transmission inhibition assay, ME180 cells were trypsinized, washed and seeded in 96-well flat bottom microtiter plates (COSTAR) at a density of $5 \times 10^3$ cells per well. The cells were incubated at 37° C. for 24 hours prior to the tart of the assay. H9 cells chronically infected with he SK1 isolate of HIV-1 were treated with 200 µg/ml mitomycin C for 60 minutes at 37° C. After treatment the cells were washed three times with tissue culture medium. The chronically infected lymphocytes were added to each well at a density of $2 \times 10^4$ cells per well. The concentration of mitomycin C used in the treatment of the lymphocytes was chosen to allow lymphocyte survival for the period of time required to transmit virus to the uninfected ME180 cells, but to die prior to the time of assay so as not to contribute to the p24 signal used as the endpoint (see below). In the transmission assay the lytic peptides D4E1 and D2A21, with and without 150 μg/ml pig mucin, were added prior to the addition of chronically infected cells or were mixed with the chronically infected cells prior to their addition to the monolayer of ME180 cells. Mucin was included because it is an abundant constituent of the normal vaginal secretions of a human being, thus any chemotherapeutic agent targeting HIV should be active in its presence if it is to have clinical value. Dextran and dextran sulfate (with and without pig mucin) were also tested as negative and positive controls, respectively. The lymphocytes and peptide were co-cultured with the ME180 cells for 6 hours and then removed by washing the ME180 monolayer four times with PBS. The plate was then incubated at 37° C. for six days. Medium was removed and changed every 48 hours during the incubation stage. No further peptide was added after the initial dose. At six days post-co-cultivation, the supernatant was removed from the wells and evaluated for the quantity of p24 antigen by ELISA. The ELISA was performed according to the manufacturer's recommendations. The amount of virus production in wells treated with various concentrations of the peptides was evaluated with appropriate cell and virus controls. Data are reported as a percent of virus control at each drug concentration. Linear regression analysis was used to calculate the $IC_{25}$ $IC_{30}$ and $IC_{95}$ concentrations of the transmission inhibitor. The results are given in Tables I through IX, below, and in FIGS. 1–9. $TC_{50}$, the concentration at which 50% of cells are eliminated, was determined by interpolation from the %CC data. TI represents the toxicity index, which is the ratio of the $TC_{50}/IC_{50}$, and is an indication of the relative concentrations window that exists between efficacy and toxicity.

TABLE I

INHIBITION OF CELL-CELL TRANSMISSION BY D4E1 p24 VALUES (μg/ml)

| CONC (μg/ml) | 0 | 0.32 | 1 | 3.2 | 10 | 32 | 100 |
|---|---|---|---|---|---|---|---|
| SAMPLE 1 | 52.5 | 21.6 | 25.9 | 27.5 | 6.5 | 1.4 | 0.0 |
| SAMPLE 2 | 59.3 | 29.1 | 28.5 | 19.2 | 2.6 | 0.0 | 0.0 |
| SAMPLE 3 | 54.4 | 26.9 | 19.2 | 17.9 | 4.9 | 4.2 | 0.0 |
| MEAN | 55.4 | 25.9 | 24.5 | 21.5 | 4.7 | 1.9 | 0.0 |
| % VC | 100.0 | 46.8 | 44.3 | 38.9 | 8.4 | 3.4 | 0.0 |
| STD DEV | 6.3 | 6.8 | 8.7 | 9.4 | 3.6 | 3.9 | 0.0 |

TOXICITY VALUES (XTT – O.D. @ 450/650 nm)

| CONC (μg/ml) | 0 | 0.32 | 1 | 3.2 | 10 | 32 | 100 |
|---|---|---|---|---|---|---|---|
| SAMPLE 1 | 0.506 | 0.518 | 0.535 | 0.510 | 0.493 | 0.551 | 0.138 |
| SAMPLE 2 | 0.526 | 0.528 | 0.523 | 0.486 | 0.526 | 0.513 | 0.162 |
| SAMPLE 3 | 0.548 | 0.516 | 0.511 | 0.513 | 0.524 | 0.524 | 0.128 |
| MEAN | 0.527 | 0.521 | 0.523 | 0.503 | 0.515 | 0.529 | 0.143 |
| % CC | 100.0 | 98.6 | 99.2 | 95.4 | 97.7 | 100.4 | 27.1 |
| STD DEV | 4.0 | 1.1 | 2.3 | 2.8 | 3.6 | 3.7 | 3.3 |

$IC_{50}$ = 0.31 μg/ml     $TC_{50}$ = 64 μg/ml     TI = 206

TABLE II

INHIBITION OF CELL-CELL TRANSMISSION BY D4E1 WITH 150 μg/ml PIG MUCIN p24 VALUES (μg/ml)

| CONC (μg/ml) | 0 | 0.32 | 1 | 3.2 | 10 | 32 | 100 |
|---|---|---|---|---|---|---|---|
| SAMPLE 1 | 52.1 | 27.0 | 14.1 | 6.7 | 0.0 | 0.0 | 0.0 |
| SAMPLE 2 | 57.3 | 15.5 | 11.8 | 3.3 | 0.0 | 0.0 | 0.0 |
| SAMPLE 3 | 59.3 | 20.2 | 14.8 | 4.7 | 5.4 | 9.4 | 0.0 |
| MEAN | 56.2 | 20.9 | 13.6 | 4.9 | 1.8 | 3.1 | 0.0 |
| % VC | 100.0 | 37.2 | 24.1 | 8.7 | 3.2 | 5.6 | 0.0 |
| STD DEV | 6.6 | 10.3 | 2.8 | 3.0 | 5.5 | 9.7 | 0.0 |

TOXICITY VALUES (XTT – O.D. @ 450/650 nm)

| CONC (μg/ml) | 0 | 0.32 | 1 | 3.2 | 10 | 32 | 100 |
|---|---|---|---|---|---|---|---|
| SAMPLE 1 | 0.506 | 0.518 | 0.535 | 0.510 | 0.493 | 0.551 | 0.138 |
| SAMPLE 2 | 0.528 | 0.528 | 0.523 | 0.486 | 0.526 | 0.513 | 0.162 |
| SAMPLE 3 | 0.548 | 0.518 | 0.511 | 0.513 | 0.524 | 0.524 | 0.128 |
| MEAN | 0.527 | 0.521 | 0.523 | 0.503 | 0.515 | 0.529 | 0.143 |
| % CC | 100.0 | 98.6 | 99.2 | 95.4 | 97.7 | 100.4 | 27.1 |
| STD DEV | 4.0 | 1.1 | 2.3 | 2.8 | 3.6 | 3.7 | 3.3 |

$IC_{50}$ = 0.29 μg/ml     $TC_{50}$ = 64 μg/ml     TI = 221

TABLE III

INHIBITION OF CELL-CELL TRANSMISSION BY D2A21 p24 VALUES (μg/ml)

| CONC (μg/ml) | 0 | 0.32 | 1 | 3.2 | 10 | 32 | 100 |
|---|---|---|---|---|---|---|---|
| SAMPLE 1 | 52.5 | 40.1 | 38.0 | 22.6 | 14.1 | 3.6 | 0.0 |
| SAMPLE 2 | 59.3 | 47.9 | 41.2 | 20.7 | 19.5 | 0.0 | 0.0 |
| SAMPLE 3 | 54.4 | 48.0 | 32.6 | 24.2 | 11.9 | 0.0 | 0.0 |
| MEAN | 55.4 | 45.3 | 37.3 | 22.5 | 15.2 | 1.2 | 0.0 |
| % VC | 100.0 | 81.8 | 67.3 | 40.6 | 27.4 | 2.2 | 0.0 |
| STD DEV | 6.3 | 8.2 | 7.8 | 3.2 | 7.1 | 3.8 | 0.0 |

TOXICITY VALUES (XTT – O.D. @ 450/650 nm)

| CONC (μg/ml) | 0 | 0.32 | 1 | 3.2 | 10 | 32 | 100 |
|---|---|---|---|---|---|---|---|
| SAMPLE 1 | 0.506 | 0.541 | 0.550 | 0.525 | 0.518 | 0.342 | 0.061 |
| SAMPLE 2 | 0.528 | 0.497 | 0.514 | 0.513 | 0.506 | 0.315 | 0.083 |
| SAMPLE 3 | 0.548 | 0.506 | 0.520 | 0.506 | 0.491 | 0.308 | 0.096 |
| MEAN | 0.527 | 0.515 | 0.528 | 0.515 | 0.506 | 0.322 | 0.087 |
| % CC | 100.0 | 97.6 | 100.1 | 97.6 | 95.9 | 61.04 | 16.4 |
| STD DEV | 4.0 | 4.4 | 3.7 | 1.8 | 2.6 | 3.4 | 1.5 |

$IC_{50} = 0.26$ μg/ml  $TC_{50} = 39$ μg/ml  TI = 15

TABLE IV

INHIBITION OF CELL-CELL TRANSMISSION BY D2A21 WITH 150 μg/ml PIG MUCIN p24 VALUES (μg/ml)

| CONC (μg/ml) | 0 | 0.32 | 1 | 3.2 | 10 | 32 | 100 |
|---|---|---|---|---|---|---|---|
| SAMPLE 1 | 62.1 | 20.1 | 20.2 | 12.2 | 7.0 | 0.0 | 0.0 |
| SAMPLE 2 | 57.3 | 21.0 | 11.7 | 12.0 | 3.3 | 0.0 | 0.0 |
| SAMPLE 3 | 59.3 | 19.1 | 17.6 | 9.4 | 7.7 | 0.0 | 0.0 |
| MEAN | 59.6 | 20.1 | 16.5 | 11.2 | 6.0 | 0.0 | 0.0 |
| % VC | 100.0 | 33.7 | 27.7 | 18.8 | 10.1 | 0.0 | 0.0 |
| STD DEV | 4.0 | 1.6 | 7.3 | 2.6 | 4.0 | 0.0 | 0.0 |

TOXICITY VALUES (XTT – O.D. @ 450/650 nm)

| CONC (μg/ml) | 0 | 0.32 | 1 | 3.2 | 10 | 32 | 100 |
|---|---|---|---|---|---|---|---|
| SAMPLE 1 | 0.506 | 0.541 | 0.550 | 0.525 | 0.518 | 0.342 | 0.081 |
| SAMPLE 2 | 0.528 | 0.497 | 0.514 | 0.513 | 0.508 | 0.315 | 0.083 |
| SAMPLE 3 | 0.548 | 0.506 | 0.520 | 0.506 | 0.491 | 0.308 | 0.096 |
| MEAN | 0.527 | 0.515 | 0.528 | 0.515 | 0.506 | 0.322 | 0.087 |
| % CC | 100.0 | 97.6 | 100.1 | 97.6 | 95.9 | 61.04 | 16.4 |
| STD DEV | 4.0 | 4.4 | 3.7 | 1.8 | 2.6 | 3.4 | 1.5 |

$IC_{50} = 02.6$ μg/ml  $TC_{50}$ 39 μg/ml  TI = 139

TABLE V

INHIBITION OF CELL-CELL TRANSMISSION BY DEXTRAN SULFATE p24 VALUES (μg/ml)

| CONC (μg/ml) | 0 | 0.32 | 1 | 3.2 | 10 | 32 | 100 |
|---|---|---|---|---|---|---|---|
| SAMPLE 1 | 55.4 | 3.1 | 8.4 | 0.0 | 0.0 | 0.0 | 0.0 |
| SAMPLE 2 | 52.9 | 0.3 | 4.0 | 0.0 | 0.0 | 0.0 | 0.0 |
| SAMPLE 3 | 55.4 | 6.2 | 0.0 | 0.0 | 0.3 | 0.0 | 0.0 |
| MEAN | 54.6 | 3.2 | 4.1 | 0.0 | 0.0 | 0.0 | 0.0 |
| % VC | 100.0 | 5.9 | 7.6 | 0.0 | 0.2 | 0.0 | 0.0 |
| STD DEV | 2.6 | 6.4 | 7.7 | 0.0 | 0.3 | 0.0 | 0.0 |

TOXICITY VALUES (XTT – O.D. @ 450/650 nm)

| CONC (μg/ml) | 0 | 0.32 | 1 | 3.2 | 10 | 32 | 100 |
|---|---|---|---|---|---|---|---|
| SAMPLE 1 | 0.519 | 0.477 | 0.479 | 0.483 | 0.463 | 0.444 | 0.479 |
| SAMPLE 2 | 0.501 | 0.473 | 0.519 | 0.456 | 0.499 | 0.466 | 0.500 |
| SAMPLE 3 | 0.504 | 0.504 | 0.501 | 0.457 | 0.497 | 0.499 | 0.495 |
| MEAN | 0.506 | 0.485 | 0.500 | 0.465 | 0.486 | 0.470 | 0.491 |

TABLE V-continued

INHIBITION OF CELL-CELL TRANSMISSION BY DEXTRAN SULFATE

| % CC | 100.0 | 95.4 | 98.4 | 91.5 | 95.7 | 92.5 | 98.7 |
|---|---|---|---|---|---|---|---|
| STD DEV | 1.9 | 3.3 | 3.9 | 3.0 | 4.0 | 5.4 | 2.2 |

| $IC_{50}$ = 0.002 µg/ml | $TC_{50}$ = 1 µg/ml | TI = 500 |
|---|---|---|

TABLE VI

INHIBITION OF CELL-CELL TRANSMISSION BY DEXTRAN SULFATE
WITH 150 µg/ml PIG MUCIN p24 VALUES (µg/ml)

| CONC (µg/ml) | 0 | 0.32 | 1 | 3.2 | 10 | 32 | 100 |
|---|---|---|---|---|---|---|---|
| SAMPLE 1 | 62.0 | 3.2 | 3.1 | 4.7 | 3.2 | 13.4 | 0.7 |
| SAMPLE 2 | 64.8 | 6.1 | 3.6 | 6.1 | 7.9 | 5.4 | 11.6 |
| SAMPLE 3 | 59.3 | 5.0 | 7.9 | 10.5 | 10.5 | 8.3 | 2.5 |
| MEAN | 62.0 | 4.5 | 4.9 | 7.1 | 7.2 | 9.0 | 4.9 |
| % VC | 100.0 | 7.7 | 7.8 | 11.4 | 11.6 | 14.6 | 8.0 |
| STD DEV | 4.4 | 2.4 | 4.3 | 4.9 | 6.0 | 6.5 | 9.4 |

TOXICITY VALUES (XTT – O.D. @ 450/650 nm)

| CONC (µg/ml) | 0 | 0.32 | 1 | 3.2 | 10 | 32 | 100 |
|---|---|---|---|---|---|---|---|
| SAMPLE 1 | 0.519 | 0.477 | 0.479 | 0.483 | 0.463 | 0.444 | 0.479 |
| SAMPLE 2 | 0.501 | 0.473 | 0.519 | 0.456 | 0.499 | 0.466 | 0.500 |
| SAMPLE 3 | 0.504 | 0.504 | 0.501 | 0.457 | 0.497 | 0.499 | 0.495 |
| MEAN | 0.506 | 0.485 | 0.500 | 0.465 | 0.486 | 0.470 | 0.491 |
| % CC | 100.0 | 95.4 | 98.4 | 91.6 | 95.7 | 92.5 | 98.7 |
| STD DEV | 1.9 | 3.3 | 3.9 | 3.0 | 4.0 | 5.4 | 2.2 |

| $IC_{50}$ = 0.002 µg/ml | $TC_{50}$ = 1 µg/ml | TI = 500 |
|---|---|---|

TABLE VII

INHIBITION OF CELL-CELL TRANSMISSION BY DEXTRAN p24 VALUES (µg/ml)

| CONC (µg/ml) | 0 | 0.32 | 1 | 3.2 | 10 | 32 | 100 |
|---|---|---|---|---|---|---|---|
| SAMPLE 1 | 55.4 | 52.2 | 53.5 | 50.3 | 45.3 | 51.9 | 52.6 |
| SAMPLE 2 | 52.9 | 52.5 | 57.0 | 47.2 | 45.7 | 53.2 | 52.0 |
| SAMPLE 3 | 55.4 | 48.2 | 53.5 | 52.2 | 46.6 | 52.0 | 50.1 |
| MEAN | 54.6 | 51.0 | 54.7 | 49.9 | 45.9 | 52.4 | 51.6 |
| % VC | 100.0 | 93.4 | 100.2 | 91.4 | 84.1 | 96.0 | 94.5 |
| STD DEV | 2.6 | 4.4 | 3.7 | 4.6 | 1.2 | 1.3 | 2.4 |

TOXICITY VALUES (XTT – O.D. @ 450/650 nm)

| CONC (µg/ml) | 0 | 0.32 | 1 | 3.2 | 10 | 32 | 100 |
|---|---|---|---|---|---|---|---|
| SAMPLE 1 | 0.519 | 0.462 | 0.425 | 0.477 | 0.468 | 0.457 | 0.481 |
| SAMPLE 2 | 0.501 | 0.463 | 0.457 | 0.453 | 0.467 | 0.438 | 0.491 |
| SAMPLE 3 | 0.504 | 0.488 | 0.450 | 0.459 | 0.467 | 0.493 | 0.519 |
| MEAN | 0.508 | 0.458 | 0.447 | 0.463 | 0.467 | 0.466 | 0.497 |
| % CC | 100.0 | 90.1 | 88.1 | 91.1 | 92.0 | 91.7 | 97.8 |
| STD DEV | 1.9 | 1.7 | 4.2 | 2.6 | 0.1 | 5.4 | 3.9 |

| $IC_{50}$ = 100 µg/ml | $TC_{50}$ = 100 µg/ml | TI = N/A |
|---|---|---|

TABLE VIII

INHIBITION OF CELL-CELL TRANSMISSION BY DEXTRAN
With 150 µg/ml PIG MUCIN p24 VALUES (µg/ml)

| CONC (µg/ml) | 0 | 0.32 | 1 | 3.2 | 10 | 32 | 100 |
|---|---|---|---|---|---|---|---|
| SAMPLE 1 | 62.0 | 53.5 | 57.5 | 54.7 | 58.1 | 60.5 | 59.6 |
| SAMPLE 2 | 64.8 | 58.9 | 50.9 | 57.3 | 61.1 | 65.1 | 70.6 |
| SAMPLE 3 | 59.3 | 56.2 | 51.0 | 52.1 | 53.2 | 65.5 | 63.7 |
| MEAN | 62.0 | 56.2 | 53.1 | 54.7 | 57.5 | 63.7 | 64.6 |

TABLE VIII-continued

INHIBITION OF CELL-CELL TRANSMISSION BY DEXTRAN

With 150 μg/ml PIG MUCIN

| % VC | 100.0 | 90.6 | 86.72 | 88.2 | 92.6 | 102.7 | 104.2 |
|---|---|---|---|---|---|---|---|
| STD DEV | 4.4 | 4.4 | 6.1 | 4.2 | 6.4 | 4.6 | 9.0 |

TOXICITY VALUES (XTT – O.D. @ 450/650 nm)

| CONC (μg/ml) | 0 | 0.32 | 1 | 3.2 | 10 | 32 | 100 |
|---|---|---|---|---|---|---|---|
| SAMPLE 1 | 0.519 | 0.462 | 0.425 | 0.477 | 0.468 | 0.467 | 0.481 |
| SAMPLE 2 | 0.501 | 0.463 | 0.467 | 0.453 | 0.467 | 0.438 | 0.491 |
| SAMPLE 3 | 0.504 | 0.448 | 0.450 | 0.459 | 0.467 | 0.493 | 0.519 |
| MEAN | 0.508 | 0.458 | 0.447 | 0.463 | 0.467 | 0.466 | 0.497 |
| % CC | 100.0 | 90.1 | 88.1 | 91.1 | 92.0 | 91.7 | 97.8 |
| STD DEV | 1.9 | 1.7 | 4 | 2 | 2.5 | 0.1 | 5.4 | 3.9 |

| $IC_{50} = 100$ μg/ml | $TC_{50} = 100$ μg/ml | TI = N/A |
|---|---|---|

TABLE IX

INHIBITION OF CELL-CELL TRANSMISSION BY PIG MUCIN

With 150 μg/ml PIG MUCIN p24 VALUES (μg/ml)

| CONC (μg/ml) | 0 | 0.32 | 1 | 3.2 | 10 | 32 | 100 |
|---|---|---|---|---|---|---|---|
| SAMPLE 1 | 52.5 | 56.5 | 52.1 | 58.7 | 54.3 | 19.5 | 0.0 |
| SAMPLE 2 | 59.3 | 53.2 | 55.2 | 59.3 | 53.0 | 28.8 | 0.0 |
| SAMPLE 3 | 54.4 | 51.3 | 50.9 | 58.4 | 62.5 | 18.9 | 0.0 |
| MEAN | 55.4 | 53.7 | 52.7 | 58.6 | 56.6 | 22.4 | 0.0 |
| % VC | 100.0 | 96.9 | 95.22 | 106.1 | 102.2 | 40.47 | 0.0 |
| STD DEV | 6.3 | 4.7 | 4.0 | 0.8 | 9.3 | 10.0 | 0.0 |

TOXICITY VALUES (XTT – O.D. @ 450/650 nm)

| CONC (μg/ml) | 0 | 0.32 | 1 | 3.2 | 10 | 32 | 100 |
|---|---|---|---|---|---|---|---|
| SAMPLE 1 | 0.506 | 0.515 | 0.537 | 0.507 | 0.513 | 0.283 | 0.143 |
| SAMPLE 2 | 0.528 | 0.548 | 0.562 | 0.516 | 0.514 | 0.304 | 0.151 |
| SAMPLE 3 | 0.548 | 0.538 | 0.536 | 0.526 | 0.524 | 0.289 | 0.147 |
| MEAN | 0.527 | 0.534 | 0.545 | 0.516 | 0.517 | 0.292 | 0.147 |
| % CC | 100.0 | 101.2 | 103.4 | 97.9 | 98.0 | 55.4 | 27.9 |
| STD DEV | 4.0 | 3.2 | 2.8 | 1.8 | 1.2 | 2.1 | 0.8 |

| $IC_{50} = 1.4$ μg/ml | $TC_{50} = 1.7$ μg/ml | TI = 1.2 |
|---|---|---|

It can be seen from this data that both peptide D4E1 and peptide D2A21 cause a significant decrease in p24, an indicator of virus level, at concentrations well below those that are toxic to normal, un-infected cells. The addition of mucin was actually found to enhance this activity, indicating that an in vivo effect comparable or better than that seen in vitro can be expected.

EXAMPLE 2

Inhibition of FIV Transmission by Lytic Peptides

Experiment design and method: To see the long term effect of a single D4E1 treatment, FIV-Petaluma chronically infected CrFK cells were treated with 2 μM D4E1, and the supernatant was collected at day 1, 3, 5, 7 and 12. P26 levels in these supernatants were measured by ELISA. To see virus infectivity after D4E1 treatment, supernatants from day 7 post-treatment by D4E1 of FIV infected CrFK cells were tested in a $TCID_{50}$ assay. Log dilutions of supernatants were made and were added to target cells, E or Fet-J cells. At the peak virus replication points (days depend on different virus and target cell type), virus infection was checked. Evidence of virus infection and virus infectious titer was indicated by p26 positive in specific dilution wells. $TCID_{50}$ were calculated according to the Reed-Muench method.

Results and discussion: The long term effect of a single D4E1 treatment of FIV p26 levels is seen in Table X FIG. 1. In this experiment, CrFK cells were incubated with 2 μM D4E1 for 1, 3, 5 and 7 days, and the supernatants were collected for $TCID_{50}$ assay. Log dilutions were made and cultured with E and Fet-J cells. For E cell infection, p26 levels of the supernatant were tested at D0, D15, D21. At day 1, p26 was drastically decreased (57% of positive control). However, p26 levels gradually recovered with prolonged culture and after day 5, were comparable to untreated cultures. The experiment indicated that a 2 μM single treatment of D4E1 can not control virus after day 3.

TABLE X

Time course of p26 level from supernatants of
single treatment of FIV-Petaluma chronically
infected CrFK cell with D4E1 p26 level (OD)

|    | D4E1 − | D4E1 + | % pos. CTL | % suppressing |
|----|--------|--------|------------|---------------|
| D0 |        |        | 100        | 0             |
| D1 | 945.5  | 541.5  | 57         | 43            |
| D3 | 2492.5 | 1830.5 | 13         | 27            |
| D5 | 3205.5 | 3412.5 | 106        | −6            |
| D7 | 3370.5 | 3515.5 | 104        | −4            |

In order to see whether the virus in day 7 supernatant were infective, a $TCID_{50}$ assay was performed. Supernatant from the D4E1 treated culture yielded almost a 2 log lower $TCID_{50}$ than supernatant from untreated cultures, despite comparable levels of p26. Table XI and FIG. 2. This result is interesting and indicates that FIV from D4E1-treated cells may be defective.

TABLE XI $TCID_{50}$ of day 7 supernatant from FIV-Petaluma
chronically infected CrFK cells treated with
or without D4E1

$TCID_{50}$ of Day 7 Supernatants

|                | D4E1 −      | D4E1 +     |
|----------------|-------------|------------|
| # virus        | 178         | 3          |
| Dilution (log) | $10^{2.25}$ | $10^{0.5}$ |

In a second experiment, CrFK cells were incubated with either 0.5 or 2 $\mu$M D4E1 for 1, 3, 5, 7 & 12 days, and the supernatants were collected for $TCID_{50}$ assay. Log dilutions were made and cultured with E and Fet-J cells. For E cells infection, p26 of supernatant were tested at D0, D14 and D21. For Fet-J cells infections, p26 of supernatant were tested at day 4 and 8. Results were similar to those of the first experiment (Tables XII and XIII and FIGS. 3 and 4), though the activity of D4E1 appeared to be less in this experiment than in the first. This is likely an artifact due to either biological variation of the cells or degradation of the peptide.

TABLE XII

Time course of p26 level from
supernatants of single treatment of FIV-
Petaluma chronically infected CrFK cell
with D4E1

% of Positive Controls

|     | 0.5 $\mu$M | 2 $\mu$M |
|-----|------------|----------|
| D0  | 100        | 100      |
| D1  | 57         | 69       |
| D3  | 100        | 79       |
| D5  | 100        | 100      |
| D7  | 100        | 92       |
| D12 | 100        | 95       |

TABLE XIII $TCID_{50}$ of day 7 supernatant from FIV-
Petaluma chronically infected CrFK cells
treated with or without D4E1

$TCID_{50}$ of Day 7 Supernatants

|                | D4E1 −     | D4E1 +      |
|----------------|------------|-------------|
| # virus        | 1585       | 240         |
| Dilution (log) | $10^{3.2}$ | $10^{2.38}$ |

---

I claim:

1. A method of reducing cell-to-cell transmission of an immunodeficiency virus comprising administering to an animal infected with an immunodeficiency virus an amount of a lytic peptide that is lethal neither to the virus nor to virus-infected cells, but that renders viral particles produced by the infected animal non-infectious.

2. The method of claim 1 wherein the immunodeficiency virus is a virus selected from the group consisting of Human Immunodeficiency Virus and Feline Immunodeficiency Virus.

3. The method of claim 1 wherein the lytic peptide is a peptide having a pleated sheet secondary conformation and no hydrophobic tail.

4. The method of claim 1 wherein the lytic peptide is selected from the group consisting of SEQ ID NO. 1 and SEQ ID NO. 2.

5. The method of claim 2 wherein the virus is Human Immunodeficiency Virus.

* * * * *

SEQUENCE LISTING

<160> NUMBER OF SEQ ID NOS: 2

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence:Synthetic
      peptide with beta-pleated sheet structure.

<400> SEQUENCE: 1

Phe Lys Leu Arg Ala Lys Ile Lys Val Arg Leu Arg Ala Lys Ile Lys
 1               5                  10                  15

Leu

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence:Synthetic
      peptide with alpha-helical structure.

<400> SEQUENCE: 2

-continued

```
Phe Ala Lys Lys Phe Ala Lys Lys Phe Lys Lys Phe Ala Lys Lys Phe
  1               5                  10                  15

Ala Lys Phe Ala Phe Ala Phe
             20
```